(12) United States Patent
Nygren et al.

(10) Patent No.: US 8,155,754 B2
(45) Date of Patent: Apr. 10, 2012

(54) METHOD FOR FABRICATION OF LOW-POLARIZATION IMPLANTABLE STIMULATION ELECTRODE

(75) Inventors: Lea A. Nygren, Bloomington, MN (US); James A. Coles, Jr., Minneapolis, MN (US); Scott J. Brabec, Elk River, MN (US); Randy G. Rose, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 505 days.

(21) Appl. No.: 11/042,649

(22) Filed: Jan. 25, 2005

(65) Prior Publication Data

US 2006/0167536 A1    Jul. 27, 2006

(51) Int. Cl.
*A61N 1/04* (2006.01)

(52) U.S. Cl. .................................................. 607/116

(58) Field of Classification Search .............. 607/121, 607/119, 122
See application file for complete search history.

(56) References Cited

U.S. PATENT DOCUMENTS

| | | | |
|---|---|---|---|
| 4,280,514 A | 7/1981 | MacGregor | |
| 4,502,492 A | 3/1985 | Bornzin | 128/785 |
| 4,506,680 A | 3/1985 | Stokes | |
| 4,649,937 A | 3/1987 | DeHaan et al. | |
| 4,677,989 A | 7/1987 | Robblee | |
| 4,679,572 A | 7/1987 | Baker, Jr. | 128/786 |
| 4,717,581 A | 1/1988 | Robblee | |
| 4,735,205 A | 4/1988 | Chachques et al. | |
| 4,762,136 A | 8/1988 | Baker, Jr. | |
| 4,784,160 A * | 11/1988 | Szilagyi | 607/116 |
| 4,860,446 A | 8/1989 | Lessar et al. | |
| 4,919,135 A | 4/1990 | Phillips, Jr. et al. | |
| 4,934,049 A | 6/1990 | Kiekhafer et al. | |
| 5,016,645 A | 5/1991 | Williams et al. | 128/784 |
| 5,074,313 A | 12/1991 | Dahl et al. | |
| 5,097,843 A | 3/1992 | Soukup et al. | |
| 5,265,608 A | 11/1993 | Lee et al. | 128/642 |
| 5,282,844 A | 2/1994 | Stokes et al. | 607/120 |
| 5,314,458 A | 5/1994 | Najafi et al. | |
| 5,318,572 A | 6/1994 | Helland et al. | |

(Continued)

FOREIGN PATENT DOCUMENTS

EP    237316 A2    9/1987

(Continued)

OTHER PUBLICATIONS

Weiland et al., "Chronic Neural Stimulation with Thin-Film Iridium Oxide Electrodes", *IEEE: Transactions on Biomedical Engineering*, Jul. 2000, 47(7):911-918.

(Continued)

*Primary Examiner* — Scott Getzow
*Assistant Examiner* — Amanda Patton
(74) *Attorney, Agent, or Firm* — Carol F. Barry

(57) ABSTRACT

A method for fabricating an implantable medical electrode includes roughening the electrode substrate, applying an adhesion layer, and depositing a valve metal oxide coating over the adhesion layer under conditions optimized to minimize electrode impedance and post-pulse polarization. The electrode substrate may be a variety of electrode metals or alloys including titanium, platinum, platinum-iridium, or niobium. The adhesion layer may be formed of titanium or zirconium. The valve metal oxide coating is a ruthenium oxide coating sputtered onto the adhesion layer under controlled target power, sputtering pressure, and sputter gas ratio setting optimized to minimize electrode impedance and post-pulse polarization.

7 Claims, 4 Drawing Sheets

U.S. PATENT DOCUMENTS

| | | | |
|---|---|---|---|
| 5,326,448 A | 7/1994 | Otten | |
| 5,360,442 A | 11/1994 | Dahl et al. | |
| 5,397,343 A | 3/1995 | Smits | 607/130 |
| 5,545,207 A | 8/1996 | Smits et al. | 607/130 |
| 5,571,158 A | 11/1996 | Bolz et al. | 607/121 |
| 5,587,200 A | 12/1996 | Lorenz et al. | |
| 5,654,030 A | 8/1997 | Munshi et al. | |
| 5,683,443 A | 11/1997 | Munshi et al. | 607/121 |
| 6,224,985 B1 | 5/2001 | Shah et al. | |
| 6,253,110 B1 | 6/2001 | Brabec et al. | 607/116 |
| 6,430,447 B1 | 8/2002 | Chitre et al. | |
| 6,430,448 B1 | 8/2002 | Chitre et al. | |
| 6,931,286 B2 * | 8/2005 | Sigg et al. | 607/120 |
| 7,022,621 B1 | 4/2006 | Zhang et al. | |
| 7,053,403 B1 | 5/2006 | Zhang et al. | |
| 7,098,144 B2 | 8/2006 | Zhang et al. | |
| 7,194,315 B1 | 3/2007 | Platt et al. | |
| 2001/0032005 A1 * | 10/2001 | Gelb et al. | 607/121 |
| 2004/0086542 A1 | 5/2004 | Hossainy et al. | |
| 2004/0111141 A1 | 6/2004 | Brabec et al. | |
| 2004/0176828 A1 | 9/2004 | O'Brien | |
| 2004/0220652 A1 | 11/2004 | Zhou et al. | |
| 2005/0049665 A1 | 3/2005 | Brabec et al. | |
| 2005/0057136 A1 | 3/2005 | Moriya et al. | |
| 2005/0131509 A1 | 6/2005 | Atanassoska et al. | |
| 2005/0183952 A1 | 8/2005 | Shimamune et al. | |
| 2005/0238686 A1 | 10/2005 | Hossainy et al. | |
| 2005/0246002 A1 | 11/2005 | Martinez | |
| 2006/0086314 A1 | 4/2006 | Zhang et al. | |
| 2006/0160304 A1 | 7/2006 | Hsu et al. | |
| 2006/0259109 A1 | 11/2006 | Zhou et al. | |
| 2007/0179374 A1 | 8/2007 | Nygren et al. | |
| 2007/0265692 A1 | 11/2007 | Koop et al. | |
| 2008/0183260 A1 | 7/2008 | Nygren | |
| 2008/0253922 A1 | 10/2008 | Trimmer et al. | |
| 2010/0084266 A1 | 4/2010 | Di Franco | |
| 2010/0137963 A1 | 6/2010 | Nygren et al. | |

FOREIGN PATENT DOCUMENTS

| | | |
|---|---|---|
| EP | 237316 A3 | 5/1988 |
| EP | 237316 B1 | 8/1993 |
| WO | WO 02/32497 | 4/2002 |
| WO | WO2004/073790 | 9/2004 |
| WO | WO/2006 081344 A1 | 8/2006 |

OTHER PUBLICATIONS

Ison et al., "Platinum and platinum/iridium electrode properties when used for extracochlear electrical stimulation of the totally deaf," *Medical and Biological Engineering & Computing*, 1987; 25(4):403-413.

Slavcheva et al., "Sputtered Iridium Oxide Films as Charge Injection Material for Functional Electrostimulation," *Journal of Electrochemical Society*, 2004; 151(7):E226-E237. Available online May 24, 2004.

\* cited by examiner

METHOD FOR FABRICATION OF LOW-POLARIZATION IMPLANTABLE STIMULATION ELECTRODE

FIELD OF THE INVENTION

The present invention relates to implantable stimulation electrodes generally and more particularly to implantable stimulation electrodes fabricated to reduce post pulse polarization.

BACKGROUND OF THE INVENTION

Following delivery of a cardiac pacing pulse by an electrode, an after-potential typically remains on the electrode which persists for a sufficient period of time thereafter, that can interfere with sensing of cardiac signals associated with tissue depolarization caused by the delivered pulse. This phenomenon has been addressed in a number of ways over the years, and quite a large variety of electrode coatings have been developed in an effort to reduce post pulse polarization effects. One of the most common approaches to reducing post pulse polarization is to provide a high surface area coating having micron or sub-micron size surface features, such as a porous sintered metallic coating as described in U.S. Pat. No. 4,280,514 issued to MacGregor, a metal oxide or nitride coating as described in U.S. Pat. No. 4,679,572 issued to Baker, U.S. Pat. No. 5,571,158 issued to Bolz et al. and U.S. Pat. No. 5,683,443 issued to Munshi et al., or a coating of platinum black, as described in U.S. Pat. No. 4,502,492 issued to Bornzin, U.S. Pat. No. 4,506,680 issued to Stokes and U.S. Pat. No. 5,282,844 also issued to Stokes, all of which patents are incorporated herein by reference in their entireties. As noted in these patents, the provision of a high surface area coating does substantially lower post pulse polarization levels. However, as a practical matter, further reduction in post pulse polarization levels is still desirable.

BRIEF SUMMARY OF THE INVENTION

The present invention is directed toward providing a low post-pulse polarization electrode having an increased surface area created by depositing a coating of ruthenium oxide (RuOx) on the electrode surface. Sputtering conditions during RuOx deposition are optimized to achieve the lowest post-pulse polarization and frequency dependent impedance response. Sputtering conditions that are optimized include target power, sputtering pressure and sputtering gas ratio.

In one embodiment, the electrode substrate is roughened and cleaned prior to applying the RuOx coating using mechanical roughening by grit blasting with an alumina oxide media. The roughened substrate is ultrasonically cleaned.

In another embodiment, a method for fabricating a low post-pulse polarization electrode includes applying an adhesion layer to the electrode surface prior to depositing the RuOx coating to prevent delamination of the RuOx coating. The adhesion layer is formed of titanium (Ti) or zirconium (Zr) and applied in a vacuum environment to prevent oxidation of the adhesion layer surface.

In another embodiment, the electrode substrate is ion etched to remove the spontaneous oxide film that forms over the electrode substrate and the RuOx coating is deposited prior to exposing the electrode to air.

DETAILED DESCRIPTION OF THE PREFERRED EMBODIMENTS

Figure 1:
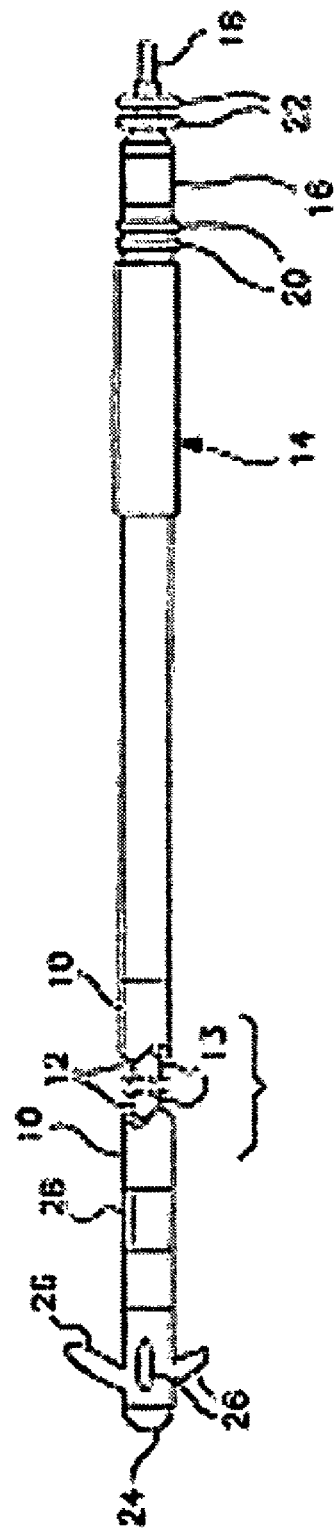
FIG. 1 is a plan view of one type of cardiac pacing lead in which the invention may usefully be practiced.

FIG. 1 is a plan view of one type of cardiac pacing lead in which the invention may usefully be practiced. In the case of FIG. 1, the lead is an endocardial pacing lead provided with an elongated insulative outer sheath 10 which carries two mutually insulated conductors 12 and 13; illustrated schematically. At the proximal end of the lead is an in-line bipolar connector assembly 14 which may correspond to the IS-1 connector standard. Connector assembly 14 is provided with a connector ring 16 coupled to conductor 12 and a connector pin 18 coupled to conductor 13. Sealing rings 20 and 22 are provided to seal the connector assembly within the bore of an associated cardiac pacemaker and to prevent fluid leakage between connector ring 16 and connector pin 18.

The proximal end of the lead carries a pacing cathode 24 and a pacing anode 28. Pacing cathode 24 may be any known type of pacing cathode employed in the context of cardiac pacing leads, however, it is illustrated as taking the general form of an endocardial pacing electrode. Tines 26 are optionally provided to assist in stabilizing electrode 24 adjacent heart tissue. The invention may be practiced with any other type of endocardial electrodes such as active fixation helical or hook type electrodes.

It should be understood in the context of the present invention that the lead of FIG. 1 is merely exemplary, and that the invention is believed useful in conjunction with any type of implantable stimulation electrode, including epicardial pacing electrodes as described, for example, in U.S. Pat. No. 5,545,207 issued to Smits et al., myocardial electrodes as described, for example, in U.S. Pat. No. 5,397,343 issued to Smits, and defibrillation electrodes as described, for example, in U.S. Pat. No. 5,016,645 issued to Williams et al. and U.S. Pat. No. 4,934,049 issued to Kiekhafer et al., all of which are incorporated herein by reference in their entireties. The invention may also be useful in the field of muscle and nerve stimulation electrodes as disclosed, for example, in U.S. Pat. No. 4,735,205 issued to Chachques et al. and U.S. Pat. No. 5,265,608 issued to Lee et al., both of which are also incorporated herein by reference in their entireties. The present invention may also be applied to subcutaneous types of electrodes or "can" or "case" electrodes incorporated in the housing of an implantable medical device. The provision of a RuOx coating to achieve improved electrical performance is believed to be beneficial in the context of all of these various implantable stimulation electrode types.

Figure 2:
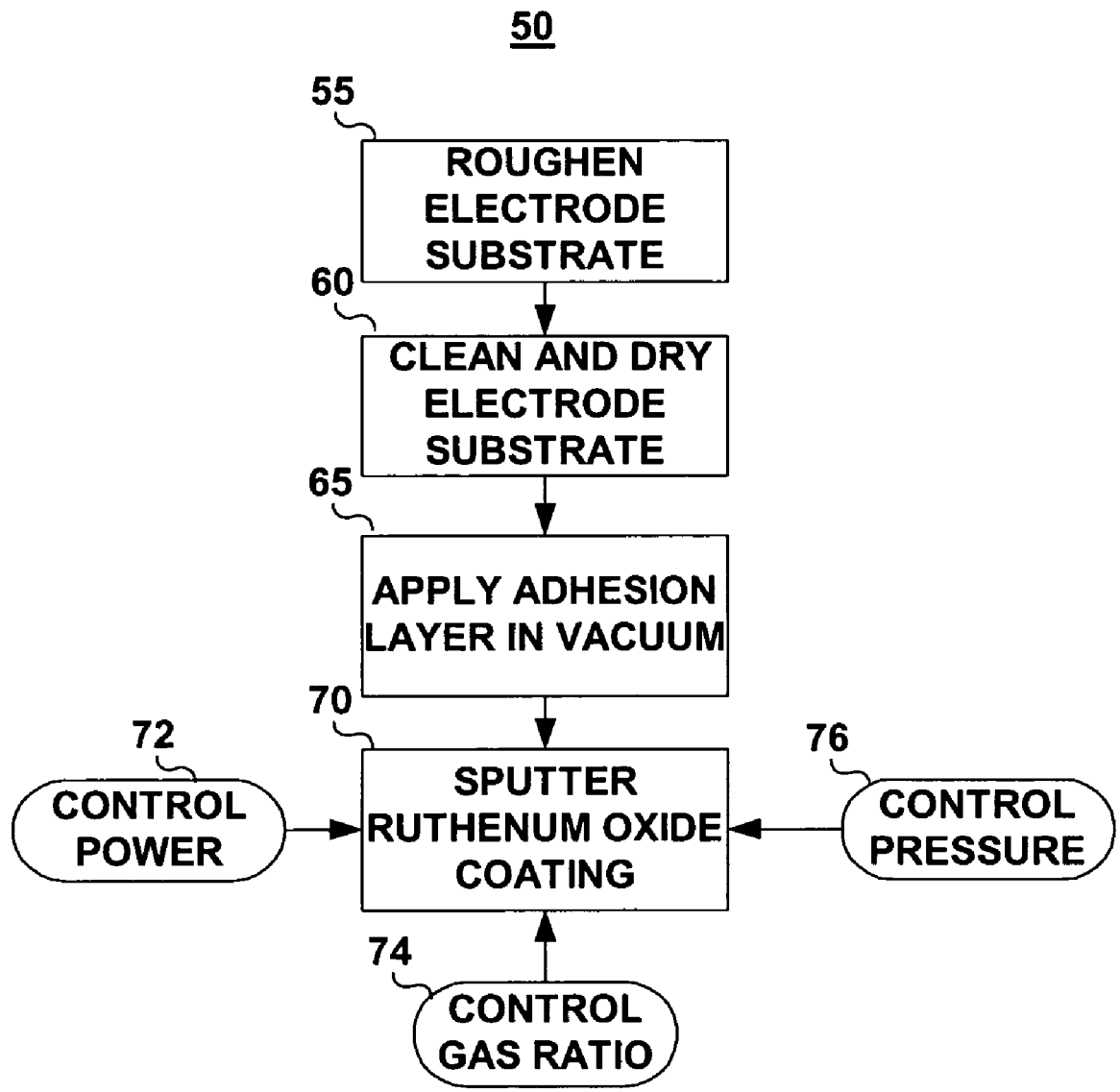
FIG. 2 is a flow chart summarizing steps included in a method for manufacturing an electrode having a RuOx coating.

FIG. 2 is a flow chart summarizing steps included in a method for manufacturing an electrode having a RuOx coating. While the embodiments described herein specify the use of RuOx, it is recognized that other metal oxide coatings, in particular valve metal oxide coatings, may achieve similar benefits in improving the electrical properties of an implantable stimulation electrode. Other oxide layer coatings may be formed from metals such as titanium, vanadium, zirconium, niobium, molybdenum, tantalum, iridium, platinum, and tungsten. The methods described for depositing a RuOx coating may therefore be similarly applied for depositing other valve metal oxide coatings on implantable stimulation electrodes.

Method 50 for fabricating a RuOx coated electrode may be applied to a variety of electrode substrate materials, such as titanium, platinum, platinum-iridium or niobium. The inventors have found that the RuOx coating develops an enhanced structure when the electrode substrate has been roughened prior to depositing the RuOx coating. The enhanced structure of the RuOx coating results in a uniform surface and an increased surface area that is expected to enhance the overall improvement in the electrical performance of the stimulation electrode.

As such, the electrode substrate is roughened at step 55. Mechanical or chemical techniques can be used to roughen the substrate surface. In an exemplary embodiment, grit blasting is used to mechanically roughen the substrate surface using an alumina oxide media. After roughening the surface, the substrate is cleaned and dried at step 60. The substrate may be cleaned using ultrasonic techniques. In experiments performed by the inventors, a grit blasted electrode substrate was cleaned ultrasonically in acetone and then in isopropyl alcohol for five minutes each and then blown dry.

Prior to depositing the RuOx coating, an adhesion layer may be applied over the roughened electrode substrate at step 65. During electrode fabrication, an oxide layer will spontaneously form over the electrode surface upon exposure to air. The presence of this oxide layer is expected to be the cause of delamination of a RuOx coating when the electrode is exposed to biphasic loads. In order to promote stronger RuOx coating adhesion, an adhesion layer is applied to the electrode substrate in a vacuum to eliminate the effects of the spontaneous oxide layer. Titanium or zirconium may be used for forming the adhesion layer. The adhesion layer may be about 500-1500 Angstroms in thickness, though other thicknesses greater than or less than this range may be effective in promoting strong adhesion of the RuOx coating. The adhesion layer may not be necessary for all applications depending on the type of stimulation pulses being applied through the electrode. Addition of the Ti adhesion layer prevented delamination of a RuOx coated electrode under biphasic loads. The adhesion layer did not alter the final electrical properties of the RuOx coated electrode.

In an alternative method, ion-etching may be performed to remove the spontaneous oxide layer from the electrode substrate in addition to or in place of applying an adhesion layer. After ion-etching, the RuOx coating is deposited without exposing the electrode substrate to air to prevent the spontaneous oxide layer from reforming.

At step 70 the RuOx coating is deposited. Deposition of the RuOx coating is performed during a sputtering process in which sputtering parameters are optimized to achieve the greatest improvement in electrical properties of the electrode. The sputtering conditions that are controlled at optimized levels to achieve the greatest improvement in electrical properties of the electrode include target power 72, total sputtering pressure 76, and the ratio of oxygen to argon in the sputter gas 74. The inventors have optimized the sputtering parameters 72, 74 and 76 in a designed experiment The effects of five levels of target power 72, three levels of sputter pressure 76 and three levels of oxygen to argon ratio 74 in the sputter gas on RuOx deposition rate and final electrical properties were measured. The highest deposition rate was achieved at a power setting of 300 Watts and was associated with the highest capacitance and lowest post-pulse polarization. Effects of sputtering pressure and gas ratio on electrical properties were less significant than the power setting, however the optimal settings tested were 9 millitorr sputtering pressure and 25% ratio of oxygen to argon in the sputter gas. In other sputtering systems, the optimal settings for the sputtering parameters for achieving optimal electrical properties may vary from these specified settings. Practice of the present invention is, therefore, not limited to any particular sputter parameter setting but is directed toward using the optimal sputter parameter settings identified for a particular sputtering system that results in the greatest improvement in electrical properties (greatest reduction in post-pulse polarization).

The sputtering time will determine the RuOx coating thickness. A thickness of about 1 to 15 microns may be deposited, however practice of the present invention is not limited to a particular coating thickness. Capacitance measurements of RuOx coatings deposited on a titanium substrate showed that capacitance increased as the RuOx coating increased.

Figure 3:
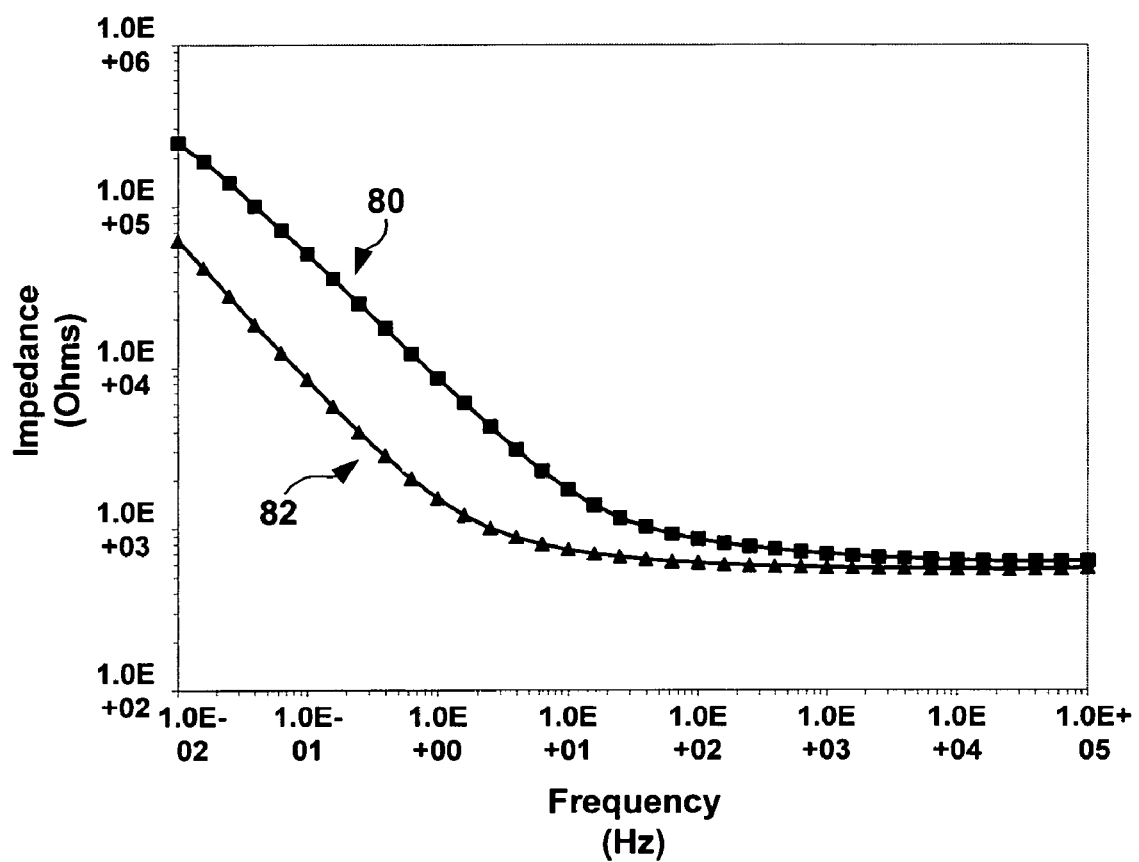
FIG. 3 is a graph of frequency-dependent impedance measured for RuOx coated PtIr electrodes.
Figure 4:
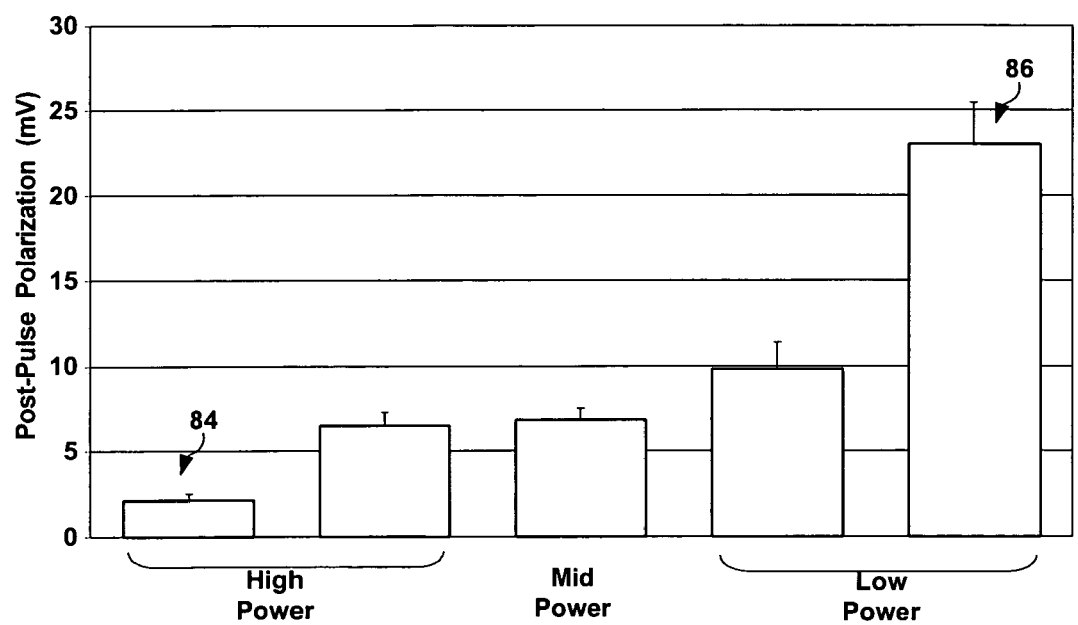
FIG. 4 is a graph of post-pulse polarization measured for RuOx coated PtIr electrodes.

FIGS. 3 and 4 illustrate the benefit of optimizing sputtering parameters for improving electrode properties. FIG. 3 is a graph of frequency-dependent impedance measured for RuOx coated PtIr electrodes. Square data points 80 correspond to impedance measurements made from a PtIr electrode coated with RuOx at a low sputtering target power setting. Triangular data points 82 correspond to impedance measurements made from a PtIr electrode coated with RuOx at a high sputtering target power setting. Lower impedances 82 were measured for the electrode coated with RuOx at a high sputtering power compared to the impedances 80 measured for the an electrode coated with RuOx at a low sputtering power.

FIG. 4 is a graph of post-pulse polarization measured for RuOx coated PtIr electrodes. Five levels of target power were tested to determine the optimal power setting. The highest power setting 84, shown at the far left, resulted in the lowest post-pulse polarization voltage and the lowest power setting 86, shown at the far right, resulted in the highest post-pulse polarization. Longer sputtering times were used for lower power settings to achieve a coating thickness of about 10 microns for all test electrodes. A thickness of about 10 microns was chosen for preparing test electrodes, however, other coating thicknesses can be beneficial in improving electrode properties.

Thus, methods for fabricating a low impedance, low-polarization electrode having a well-adhered valve-metal oxide coating have been described. Application of the methods described herein may benefit numerous types of implantable electrical devices, and therefore the exemplary embodiments described should not be considered limiting with regard to the following claims.

What is claimed is:

1. An implantable medical electrode, comprising:
   an electrode substrate roughened using a mechanical, non-chemical technique,
   an adhesion layer covering at least a portion of the mechanically-roughened electrode substrate, and
   an outer valve metal oxide coating comprising ruthenium oxide covering the adhesion layer to minimize post-pulse polarization voltage of the electrode,
   the adhesion layer preventing delamination of the outer valve metal oxide coating during application of an electrical load.

2. The electrode of claim 1 wherein the adhesion layer being a layer of one of titanium and zirconium.

3. The electrode of claim 1 wherein the adhesion layer being less than about 1500 angstroms in thickness.

4. The electrode of claim 3 wherein the valve metal oxide coating is up to about 15 microns in thickness.

5. The implantable medical electrode of claim 1 wherein the electrode comprises an active fixation hook type electrode.

6. An implantable medical electrode, comprising:
an electrode substrate roughened using a mechanical, non-chemical technique,
a layer consisting of one of titanium and zirconium, the layer covering the mechanically-roughened electrode substrate to eliminate the effects of spontaneous oxide layer formation on the electrode substrate, and
a ruthenium oxide coating covering the layer to minimize post-pulse polarization voltage of the electrode,
the layer preventing delamination of the ruthenium oxide coating during application of an electrical biphasic load.

7. An implantable medical electrode, comprising:
an electrode substrate, wherein the electrode substrate is a grit-blasted mechanically-roughened electrode substrate,
an adhesion layer covering at least a portion of the mechanically-roughened electrode substrate, and
an outer valve metal oxide coating comprising ruthenium oxide covering the adhesion layer to minimize post-pulse polarization voltage of the electrode,
the adhesion layer preventing delamination of the outer valve metal oxide coating during application of an electrical load.

* * * * *